(12) United States Patent
Burgfels et al.

(10) Patent No.: US 9,511,361 B2
(45) Date of Patent: Dec. 6, 2016

(54) SPHERICAL ZEOLITIC CATALYST FOR CONVERTING METHANOL INTO OLEFINS

(75) Inventors: Götz Burgfels, Bad Aibling (DE); Manfred D. Frauenrath, Grosskarolinenfeld (DE); Nadine Fromm, Grosskarolinenfeld (DE); Angelika Glienke, Burgkemnitz (DE); Martin Rothämel, Franfurt am Main (DE); Sven Pohl, Frankfurt am Main (DE)

(73) Assignees: CLARIANT PRODUKTE (DEUTSCHLAND) GMBH, Frankfurt am Main; AIR LIQUIDE GLOBAL E&C SOLUTIONS GERMANY GMBH, Frankfurt am Main ( * ) Notice: Subject to any disclaimer, the term of this patent is extended or adjusted under 35 U.S.C. 154(b) by 477 days.

(21) Appl. No.: 13/509,087

(22) PCT Filed: Nov. 16, 2010

(86) PCT No.: PCT/EP2010/067587
§ 371 (c)(1),
(2), (4) Date: Jun. 11, 2012

(87) PCT Pub. No.: WO2011/061196
PCT Pub. Date: May 26, 2011

(65) Prior Publication Data
US 2012/0253090 A1    Oct. 4, 2012

(30) Foreign Application Priority Data

Nov. 19, 2009  (DE) .................. 10 2009 053 922

(51) Int. Cl.
| | |
|---|---|
| C07C 1/20 | (2006.01) |
| B01J 29/06 | (2006.01) |
| B01J 37/00 | (2006.01) |
| B01J 29/40 | (2006.01) |
| B01J 35/02 | (2006.01) |
| B01J 35/08 | (2006.01) |
| B01J 35/10 | (2006.01) |

(52) U.S. Cl.
CPC ............. *B01J 37/0018* (2013.01); *B01J 29/40* (2013.01); *B01J 35/023* (2013.01); *B01J 35/08* (2013.01); *B01J 35/1019* (2013.01); *B01J 35/1023* (2013.01); *B01J 35/1038* (2013.01); *B01J 35/1042* (2013.01); *C07C 1/20* (2013.01); *B01J 35/109* (2013.01); *B01J 37/0009* (2013.01); *B01J 37/0063* (2013.01); *B01J 2229/42* (2013.01); *C07C 2529/06* (2013.01); *C07C 2529/40* (2013.01); *Y02P 20/52* (2015.11)

(58) Field of Classification Search
USPC ......... 502/60, 63, 64, 77, 8, 9; 585/639, 640
See application file for complete search history.

(56) References Cited

U.S. PATENT DOCUMENTS

| | | | |
|---|---|---|---|
| 2,620,314 A | 12/1952 | Hoekstra | |
| 3,702,886 A | 11/1972 | Argauer et al. | |
| 4,025,572 A | 5/1977 | Lago | |
| 4,861,937 A | 8/1989 | Baacke et al. | |
| 5,063,187 A | 11/1991 | Burgfels et al. | |
| 5,614,079 A * | 3/1997 | Farnos et al. | 208/27 |
| 7,224,409 B2 * | 5/2007 | Chin et al. | 348/732 |
| 7,229,941 B2 * | 6/2007 | Burgfels et al. | 502/64 |
| 2004/0138053 A1 | 7/2004 | Burgfels et al. | |
| 2004/0198586 A1 * | 10/2004 | Mohr et al. | 502/60 |
| 2006/0161035 A1 | 7/2006 | Kalnes et al. | |
| 2007/0135637 A1 * | 6/2007 | Bosch et al. | 544/352 |
| 2008/0221326 A1 * | 9/2008 | Bosch et al. | 544/352 |
| 2009/0088595 A1 * | 4/2009 | Pigeat et al. | 585/653 |
| 2011/0144335 A1 * | 6/2011 | Bosch et al. | 544/352 |
| 2012/0000819 A1 * | 1/2012 | Matsushita | 208/111.01 |

FOREIGN PATENT DOCUMENTS

| | | |
|---|---|---|
| DE | 10027159 A1 | 12/2001 |
| EP | 0123449 A1 | 10/1984 |
| EP | 0173901 A2 | 3/1986 |
| EP | 0448000 A1 | 9/1991 |
| EP | 0507122 A2 | 10/1992 |
| EP | 1138659 A1 | 10/2001 |
| EP | 2082801 A1 | 7/2009 |
| GB | 1601915 | 11/1981 |

OTHER PUBLICATIONS

Wijngaarden et al., "Industrial Catalysis: Optimizing Catalysts and Processes", pp. 25-58, 2008.*
English Translation of International Preliminary Report on Patentability, dated Jun. 12, 2012, and accompanying Written Opinion with respect to International Application No. PCT/EP2010/067587.
English Translation of German Patent Office Official Communication, dated May 23, 2012, with respect to German Patent Application No. 10 2009 053 922.0.
International Search Report, dated Jan. 28, 2011, with respect to International Application No. PCT/EP2010/067587.

* cited by examiner

*Primary Examiner* — Elizabeth Wood
(74) *Attorney, Agent, or Firm* — Scott R. Cox

(57) ABSTRACT

A catalyst containing a pentasil-type alumosilicates and a binder, in the form of spheres having an average diameter between 0.3 and 7 mm, wherein the BET surface area of the catalyst ranges from 300 to 600 m²/g. Also disclosed is a method for producing the catalyst, wherein primary crystallites of the aluminosilicate having an average diameter of at least 0.01 μm and less than 0.1 μm are mixed with the binder, shaped into spheres having an average diameter between 0.3 and 7 mm, and subsequently calcined. Also disclosed is the use of the catalyst for converting methanol into olefins, in particular propylene. Also disclosed is a method for producing olefins from methanol, in which a feed gas is fed across the catalyst.

12 Claims, 1 Drawing Sheet

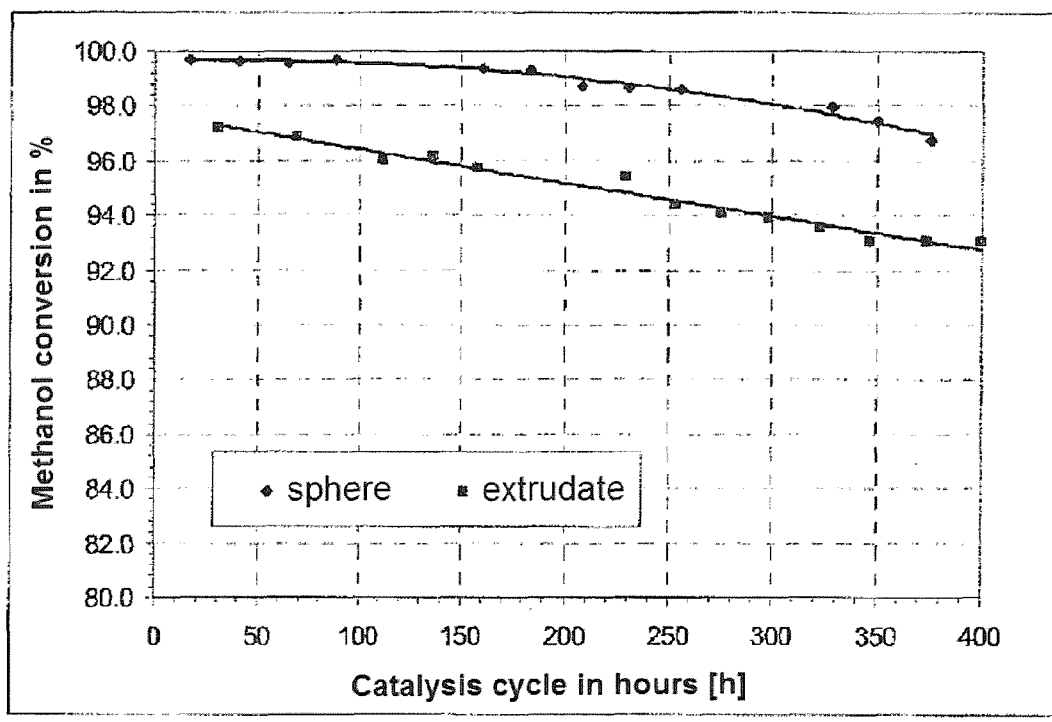

SPHERICAL ZEOLITIC CATALYST FOR CONVERTING METHANOL INTO OLEFINS

The present invention relates to a catalyst based on pentasil-type aluminosilicates, in the form of spheres with an average diameter of between 0.3 and 7 mm, wherein the BET surface area of the catalyst is between 300 and 600 $m^2/g$ and a binder is contained. The invention further relates to a process for producing the catalyst according to the invention, as well as its use for converting methanol to olefins, in particular to propylene. The present invention also relates to a process for producing olefins from methanol.

Zeolite catalysts are used to convert hydrocarbons on an industrial scale. Catalysts based on crystalline aluminosilicates which are produced from an aluminium source, a silicon source, an alkali source, a template (e.g. a tetrapropylammonium compound) and water, are known for example from U.S. Pat. No. 3,702,886.

The size of the primary crystallites of catalysts is regarded as important for the life of the catalysts. However, these primary crystallites are not customarily used directly as fine powder, but shaped into larger particles in order that they are better suited to use in catalysis processes. It is of great importance here that the reaction parameters in the reactor, for example a fixed-bed reactor, can be optimized. The reaction parameters depend on the properties of the catalysts, in particular their catalytic properties and flow properties, if for example a catalyst bed is used. EP-A-173 901 relates to a process for producing small ZSM-5-type zeolite crystallites with a $SiO_2/Al_2O_3$ molar ratio of more than 5, corresponding to a Si/Al atomic ratio of more than 2.5. The smallest dimension of the crystallites is less than 0.3 µm. The crystallites are subjected to an ion exchange reaction and shaped to larger particles after mixing with a matrix material. These are dried and calcined, wherein catalysts for different hydrocarbon conversion reactions are obtained.

The production of methanol conversion catalysts based on crystalline aluminosilicates is also described in DE-A-28 22 725. The diameter of the primary crystallites of the catalysts described there is 1 µm and more. In contrast, EP 1 424 128 relates to catalysts from crystalline aluminosilicate with primary crystallites with an average diameter of at least 0.01 µm and less than 0.1 µm, which are combined to form agglomerates of 5 to 500 µm, wherein the primary crystallites or agglomerates are bonded together by finely divided aluminium oxide. The thus-obtained catalyst material is then extruded in an extruder customary in the trade to form shaped bodies with a diameter of approximately 1.5 mm and a length of 3 mm.

EP 0 369 364 B1 relates to catalysts based on pentasil-type crystalline aluminosilicates with a Si/Al atomic ratio of at least 10, which are constructed from primary crystallites with an average diameter of at least 0.1 µm and at most 0.9 µm. The same applies to EP 0 448 000 A1. A methanol-to-olefin process and an olefin-to-diesel process are given as application examples.

EP-A-123 449 describes a process for converting alcohol or ethers to olefins using steam-treated zeolite catalysts; they have a crystal size of less than 1 µm and can be incorporated into a matrix. Clays, silicic acid and/or metal oxides are given as matrix materials.

U.S. Pat. No. 4,025,572 relates to a process for producing specific hydrocarbon mixtures, wherein the catalyst bed contains a zeolite, among other things. The synthesis of the zeolites is carried out in the presence of sulphuric acid and using $Al_2(SO_4)_3 \cdot xH_2O$. According to one example, the zeolite catalyst is mixed with 90 wt.-% aluminium oxide and pelletized.

Previously known catalysts based on zeolites with ZSM-5 structure customarily display methanol conversion activities in the cycle, starting from approx. 97%-99% (starting activity), which decrease due to the deactivation of the catalyst to values less than 80% methanol conversion with a cycle duration of more than 400 hours HOS (hours-on-stream). The catalyst must then be regenerated and is not available for further catalytic conversions during this regeneration time. At the end of the life of the catalyst, the latter can no longer be economically operated and regenerated, but must be replaced by a fresh catalyst.

The methanol conversion rates achievable over the cycle length therefore deteriorate with comparatively short cycle lengths and increased deactivation of the catalyst. Although the previously known catalysts sometimes display a high activity and selectivity as well as a very good cycle life during the catalysis process, there is a constant need for improved catalysts in order to optimize the profitability of olefin production processes.

It is therefore an object of the present invention to provide novel catalysts based on crystalline highly active aluminosilicates, which display a high activity and selectivity, and moreover an increased cycle life during the catalysis process, in catalytic processes, in particular in CMO (conversion of methanol to olefin) processes or methanol-to-propylene (MTP) conversion processes.

This object is achieved by the catalysts defined in the claims and the use according to the invention of the catalysts for converting methanol to olefins, in particular to propylene.

Within the framework of the present invention, it was unexpectedly established that catalysts based on pentasil-type aluminosilicates for converting methanol to olefins, in particular to propylene, in the form of spheres with an average diameter of between 0.3 and 7 mm, are less subject to deactivation and thus the cycle life and the total life of the catalysts can be increased. Surprisingly, the catalysts according to the invention achieve an increased temporal cycle limit. The life of the catalyst in the cycle is therefore much longer than that of known catalysts which are used in the form of extrudates (see examples). Furthermore, the catalysts according to the invention still have a methanol conversion rate of at least 94% after 400 HOS.

The catalyst according to the invention based on pentasil-type aluminosilicates is used in the form of spheres with an average diameter of between 0.3 and 7 mm, preferably between 0.5 and 5 mm, further preferably between 1 and 3.5 mm, further preferably between 2 and 3 mm and particularly preferably between 2.2 and 2.8 mm. It is also preferred that at least 20%, further preferably at least 40%, further preferably at least 60%, still further preferably at least 80%, further preferably at least 90% and most preferably at least 98% of the spheres have a diameter of between 0.3 and 7 mm, preferably between 0.5 and 5, further preferably between 1 and 3 mm, particularly preferably between 2 and 3 mm and most preferably between 2.2 and 2.8 mm. Further preferably, at least 40%, further preferably at least 60%, still further preferably at least 80%, further preferably at least 90% and most preferably 98% of the spheres (each taken individually) has a diameter which differs from the average diameter of all the spheres by at most 2 mm, further preferably by at most 1.5 mm, further preferably by at most 1.0 mm, still further preferably by at most 0.8 mm, further preferably by at most 0.6 mm, further preferably by at most 0.4 mm and most preferably by at most 0.2 mm.

The aluminosilicate suitable according to the invention can be produced in any way, for example in an aqueous reaction mixture containing a silicon source, an aluminium source, an alkali source and optionally a template. An alkali aluminosilicate gel is produced in a manner known per se, at increased temperature and optionally at increased pressure, and converted to a crystalline aluminosilicate, wherein however the reaction is terminated when the obtained primary crystallites have an average diameter of at least 0.01 μm, but less than 0.1 μm, preferably from 0.01 to 0.06 μm, in particular from 0.015 to 0.05 μm. A process for producing crystalline aluminosilicate is known for example from EP 1 424 128.

During the production of the primary crystallites, these can sometimes combine to form agglomerates which however are only loosely bonded to one another, such as for example in filter cakes. The primary crystallites can be relatively easily recovered from these if needed, e.g. by dispersion of the filter cake in an aqueous medium and by stirring the dispersion.

The average diameter of the primary crystallites is defined as the arithmetic mean averaged over a plurality of crystallites between the largest and the smallest diameter of an individual crystallite, determined using scanning electron microscopic examinations at a magnification of 20,000 (magnifications of e.g. 80,000 or also 10,000 can likewise be used, see the method section below). This definition is important in the case of crystallites with an irregular crystal habit, e.g. with rod-shaped crystallites. In the case of spherical or approximately spherical crystallites the largest and the smallest diameter coincide. The method for determining the diameters of the primary crystallites is described in the method section.

The thus-obtained primary crystallites or agglomerates thereof can then be shaped into spheres using a binder and optionally a burnout substance. Processes for this are known to a person skilled in the art and comprise for example granulation processes (for example in a pelletizer disk or Eirich mixer), spray-drying processes, gelation processes such as for example the oil-drop process and shaping processes using compression extruders.

A preferred process for producing spheres is granulation (pelletizing) in a pelletizer disk or Eirich mixer. During production in an Eirich mixer, powdery constituents (e.g. zeolite powder and burnout substance) are brought into contact with a liquid component (e.g. binder suspension) and mixed intensively, whereby spherical granules form. The obtained spheres are then dried and calcined.

Further preferably, the so-called oil-drop process can be used. In this process, a droplet coagulation (gelation) takes place starting from a metastable sol which is suspended in a different liquid phase, wherein a gelation, aging and shaping take place simultaneously. In the process, a customarily aqueous sol is converted with the help of an atomizer into droplet form, wherein the size of the atomizer nozzles is chosen according to the desired sphere diameter. The produced droplets are passed through a heated solvent immiscible with water (e.g. 100° C. oil) and settle in same as a result of the immiscibility. Due to the surface tension, gel spheres form which are dried after aging. This process is accordingly suitable for producing microspheres or spheres with a diameter of a few millimeters, such as e.g. silicon dioxide-aluminium dioxide microspheres which are used in the "Thermofor Catalytic Cracking" TCC process. The important parameters which can be varied during the oil-drop process include in particular composition of the sol, nature of the continuous phase (wherein here the density and surface tension, among others, are important), temperature, pH and contact time. Depending on the specific density, injection can be from the top or from the bottom of the column, and the process is accordingly called the "oil-drop" or "oil-up" process.

An application of the oil-drop process for producing spherical alumina is described in DE 1006406, which is hereby incorporated by reference into the present description. An acid alumina hydrosol is mixed with a gelling agent which acts as a weak base and releases ammonia as the temperature increases. This mixture is added dropwise to a hot oil bath, as a result of which the drops of the oil-insoluble mixture of alumina hydrosol/gelling agent assumes a spherical form and a gelation of the spherical particles occurs. The obtained spheres are then aged, washed and dried.

Further preferably, the shaping method can be used with compression extruders for producing spheres from two half-shells. In this production, powdery constituents (e.g. zeolite powder and burnout substance) are brought into contact with a liquid component (e.g. binder suspension and/or release agent), mixed intensively and pressed into two converging cylindrical rolls with milled-out half-shells, whereby spheres of one magnitude form. The obtained spheres are then dried and calcined.

Binders suitable according to the invention for producing the spherical catalysts are for example inorganic oxides, more preferably aluminium oxide, magnesium oxide, titanium oxide, zinc oxide, niobium oxide, zirconium oxide or silicon oxide, as well as mixtures thereof, as well as amorphous aluminosilicates and non-oxidic binders such as for example aluminium phosphates. Aluminium oxide is preferably used. Modified aluminium oxide such as for example phosphorous-modified aluminium oxide can likewise be used. The use of finely divided aluminium oxide binder which is preferably obtained by hydrolysis of aluminium trialkylene or aluminium alcoholates or is used in the form of peptizable hydrous aluminium oxide is particularly preferred. Peptizable hydrous aluminium oxide is quite particularly preferably used as binder. Further preferably, at least 95% of the particles of the peptizable hydrous aluminium oxide (relative to the average diameter) are ≤55 μm.

It is further preferred to use the binder in a quantity of 5 to 60 wt.-%, even more preferably 10 to 40 wt.-%, relative to the total weight of aluminosilicate and binder.

When producing spheres according to a granulation process, burnout substances are preferably used. Burnout substances are pore-forming substances by which in known manner the porosity and pore structure of shaped catalysts can be set in a targeted way, by adding so-called temporary additives (burnout substances) to the plasticized catalyst material before shaping, which are then removed again by thermal treatment of the shaped body. Such pore-forming substances are for example natural and synthetic organic polymers, polypeptides, polysaccharides such as for example woodchips, coconut shells, waxes, polystyrene or polyvinylidene chloride. Graphite, sugar, starch and urea can be named as further pore-forming additives or burnout substances (D. Kerner, M. Rochina, in Handbook of Heterogeneous Catalysis, G. Ertl, H. Knözinger, F. Schüth, J. Weitkamp (Edts.), Second Edition, Vol. 1, p. 286).

The construction of the spheres of the finished catalyst comprising primary crystallites, agglomerates and binders also determines the BET surface area, the pore volume as well as the pore diameter. The BET surface area of the finished catalyst in the form of spheres is determined as described in the method section, and is between 300 and 600 m²/g, further preferably 330 to 450 m²/g, particularly preferably between 350 and 420 m²/g. The pore volume of the finished catalyst in the form of spheres is determined as described in the method section, and is preferably between 0.2 and 0.8 cm³/g, more preferably between 0.25 and 0.7 cm³/g, and particularly preferably between 0.28 and 0.6 cm³/g. Furthermore, in addition preferably at least 10%, by preference at least 20%, and in particular at least 60% of the pores of the finished catalyst in the shape of spheres have a diameter of 14 to 1750 nm, preferably 80 to 1750 nm.

Within the framework of the present application, in numerical ranges such as for example "between 300 and 600" the end-points 300 and 600 are to be regarded as also disclosed and forming part of the invention.

The average diameter of the catalyst spheres is defined as the arithmetic mean averaged over a plurality of spheres.

The values described above for the BET surface area, the pore volume and the diameter of the spheres of the catalyst represent, optionally in combination with the pore diameter, an optimum selection in order to obtain catalysts with high activity and selectivity, and long life.

The present invention also relates to a process for producing the catalyst according to the invention, in which primary crystallites with an average diameter of at least 0.01 μm and less than 0.1 μm or agglomerates thereof have a binder and are optionally mixed with a burnout substance and shaped into spheres with an average diameter of between 0.3 and 7 mm, and wherein a drying and a calcining of the catalyst is then carried out. Suitable processes for forming spherical particles comprise in particular granulation processes (for example in a pelletizer disk or Eirich mixer), spray-drying processes, gelation processes such as for example the oil-drop process and shaping processes using compression extruders.

The process according to the invention for producing the catalyst according to the invention is preferably carried out as described below.

(a) in an aqueous reaction mixture containing a silicon source, an aluminium source, an alkali source and optionally a template, an alkali aluminosilicate gel is produced in a manner known per se at increased temperature and optionally at increased pressure and converted to a crystalline aluminosilicate, wherein however the reaction is terminated when the obtained primary crystallites have an average diameter of at least 0.01 μm, but less than 0.1 μm, preferably from 0.01 to 0.06 μm, in particular from 0.015 to 0.05 μm;
(b) the primary crystallites are separated from the aqueous reaction medium as pre-agglomerates, optionally after the addition of a flocculant to the aqueous medium from stage (a), dried and subjected to an intermediate calcining;
(c) in order to exchange the alkali ions in aqueous medium for a proton-containing substance or a substance that yields protons when heated, the product from stage (b) is reacted, separated off, dried, and optionally subjected anew to an intermediate calcining, whereupon an agglomerate fraction of approximately 5 to 500 μm in the form of a powder is separated off;
(d) the powder from stage (c) is mixed with a binder, preferably hydrous aluminium oxide, and optionally a burnout substance and converted into spheres with the diameter according to the invention by means of a suitable process, preferably granulation processes (for example in a pelletizer disk or Eirich mixer), spray-drying processes, gelation processes such as for example the oil-drop process and shaping processes using compression extruders;
(e) the product from stage (d) is subjected to a drying and a final calcining.

The importance of the individual stages by which the catalyst according to the invention can be obtained is explained in further detail below:

In stage (a) an aqueous reaction mixture containing a silicon source (for example colloidal silicic acid or an alkali silicate), an alkali and an aluminium source (alkali aluminate, in particular sodium aluminate) and a template, is produced first. According to the invention, there is no (separate) addition of acid in stage a) (primary synthesis of the crystalline aluminosilicates). In particular, compared with known processes, no mineral acids such as sulphuric acid are used in the reaction mixture during the primary synthesis. The problems that arise when handling (strong) acids are avoided and advantageous catalysts are also obtained.

If the catalyst according to a particularly preferred embodiment according to the invention is to be used in a CMO or MTP process, in particular a process according to DE 100 27 159 A1, the disclosure therein regarding same is hereby incorporated into the description, the percentages by weight between silicon source and aluminium source are chosen such that crystalline aluminosilicates with a Si/Al atomic ratio between approximately 50 and 250, preferably approximately 50 and 150, in particular approximately 75 to 120 are obtained.

An alkali aluminosilicate gel is produced in a manner known per se from the reaction mixture at increased temperature and optionally at increased pressure. It is already possible to operate at temperatures starting from 90° C., but the reaction times in this case are comparatively long (approximately 1 week). Therefore temperatures of 90 to 190° C., in particular from 90 to 150° C. are preferably used, wherein at temperatures of more than 100° C. (under normal conditions) excess pressure is automatically established depending on the temperature.

The aluminosilicate gel is converted to a crystalline aluminosilicate in the course of the reaction. If the temperature of the reaction mixture is higher than 190° C., the growth of the aluminosilicate primary crystallites is too rapid and primary crystallites that are too large are readily obtained, while simultaneously aluminosilicate gel is still present in the reaction mixture.

Tetraalkylammonium compounds, preferably tetrapropylammonium hydroxide (TPAOH) or tetrapropylammonium bromide (TPABr) are used as templates. Mixtures of ammonia or an organic amine and a further organic compound from the group of alcohols, preferably butanol, can also be used as templates.

The aqueous reaction mixture from stage (a) preferably has a pH of 10 to 13. At a pH of less than 10, the conversion of the aluminosilicate gel to the crystalline aluminosilicate proceeds comparatively slowly. At pH values higher than 13 the aluminosilicate crystals can in some cases dissolve again.

The formation of the crystalline aluminosilicate primary crystallites can be controlled by suitable selection of the silicon source, the aluminium source, the alkali source and the template as well as by suitable selection of the temperature and of the pH and stirring speed. Essential is that the reaction is terminated when the primary crystallites have reached the desired average diameter.

To this end, several test runs are carried out. After only a few tests the optimum parameters on the basis of which the required size ranges of the primary crystallites are reached can be ascertained. A further sign of the end of the reaction is that the pH of the reaction mixture suddenly increases.

According to the invention, it is not necessary for a new reaction mixture to be produced in each case. Instead, in order to produce the aluminosilicate gel, the silicon source, the alkali source, the aluminium source, the template and the water from the mother liquors of previous syntheses can be used and supplemented by the quantities of the named compounds required for the synthesis of the aluminosilicate gel.

The formation of the aluminosilicate primary crystallites from stage (a) preferably takes place at a pH between 10 and 13, wherein the reaction mixture is stirred. In this way, the size distribution of the primary crystallites is homogenized. However, the stirring speed is preferably to be no more than 900 rpm. At higher stirring speeds the proportion of smaller primary crystallites is higher, which may be advantageous provided that it is ensured that the average diameter of all the primary crystallites is at least 0.01 µm.

In stage (b), the primary crystallites are separated from the aqueous reaction medium as pre-agglomerates, i.e. not as individual crystallites. This is preferably achieved by adding a flocculant to the aqueous reaction medium. In general, a cationic organic macromolecular compound is used as flocculant.

The flocculant not only facilitates the separation off of the primary crystallites from the reaction medium (improved filterability), but also causes the primary crystallites to combine to form pre-agglomerates which are already largely equivalent in terms of size, structure and accumulation of the primary crystallites to the agglomerates formed in the subsequent stage. The pre-agglomerates are dried and subjected to an intermediate calcining, which is first preferably carried out in an inert atmosphere at approximately 200 to 350° C., in particular at approximately 250° C., wherein one part of the template is broken down.

The intermediate calcining can then be completed in an oxidizing atmosphere at approximately 350 to 600° C., wherein any residual quantity of template still present is burnt off.

In general, the pre-agglomerates are subjected to intermediate calcining for approximately 1 to 20 hours in the inert atmosphere and approximately 1 to 30 hours in the oxidizing atmosphere.

In stage (c), in order to exchange the alkali ions in aqueous medium for a proton-containing substance or a substance that yields protons when heated, the product from stage (b) is reacted. For example, the ion exchange can be carried out with the help of a diluted mineral acid (e.g. hydrochloric acid, nitric acid or sulphuric acid) or an organic acid (e.g. acetic acid). The ion exchange is preferably carried out accompanied by stirring for at least an hour at temperatures between 25 and 100° C., wherein at least some of the alkali ions in the pre-agglomerates of the primary crystallites are exchanged for hydrogen ions. If necessary, the ion exchange can be repeated under the same conditions.

After the exchange of the alkali ions in aqueous medium, the product containing protons (H zeolite) is separated off (for example by filtration), dried and optionally subjected to an intermediate calcining. The intermediate calcining is carried out at temperatures of 400 to 800° C., preferably at approximately 600° C. over a period of 5 to 20 hours.

As an alternative to the diluted acid, the ion exchange can also be carried out using an ammonium salt solution under comparable conditions. In this case, the alkali ions are exchanged for ammonium ions. If the thus-obtained product is subjected to an intermediate calcining, ammonia is removed and a product containing protons is obtained.

The powdery product obtained after the drying and optionally an intermediate calcining contains on the one hand agglomerates which are ≥500 µm, and on the other hand dust portions which are ≤5 µm. An agglomerate fraction of approximately 5 to 500 µm is therefore separated off.

In stage (d), this agglomerate fraction is mixed with the binder and optionally the burnout substance, wherein preferably at least 95% of the particles of the binder are ≤55 µm and at least 30% are ≥35 µm. These values, averaged over a plurality of particles, are each relative to the average diameter which is defined as the average diameter of the primary crystallites. In particular, the binder, preferably the aluminium oxide, typically has the following particle size distribution: 99%≤90 µm; 95%≤45 µm; 55%≤25 µm.

The binder is substantially responsible for setting the pore volume of the catalyst according to the invention. According to the invention, the quantity of finely divided hydrous aluminium oxide binder that is preferably to be used is approximately 5 to 60 wt.-%, relative to the total weight of the product (the mixture) from stage (d). The finely divided hydrous aluminium oxide binder is preferably peptizable aluminium oxide which has a particularly low Na and Fe content.

Preferably, in order to peptize the hydrous aluminium oxide, an acid concentration of 0.01 to 2.5 mol $H^+$/mol $Al_2O_3$, preferably from 0.02 to 1.5 mol $H^+$/mol $Al_2O_3$, still more preferably from 0.05 to 1.0 mol $H^+$/mol $Al_2O_3$ and in particular from 0.1 to 0.8 mol $H^+$/mol $Al_2O_3$ is set.

The peptizing can in principle be carried out with organic or inorganic acids in a concentration range of the acid of 0.1% to 100%. For example, organic acids such as 100% acetic acid or diluted organic acids such as 52% nitric acid etc. can be used.

In stage (d), the mixture comprising the agglomerate fraction and the binder is converted into spheres according to processes known to a person skilled in the art. Suitable processes comprise in particular granulation processes (for example in a pelletizer disk or Eirich mixer), spray-drying processes, gelation processes such as for example the oil-drop process and shaping processes using compression extruders, as discussed in detail above.

In stage (e), the product from stage (d) is then subjected to a drying and final calcining. In general, this can be carried out for 1 to 12 hours at temperatures of between approximately 350° C. and 850° C., preferably between approximately 500° C. and 850° C. However, within the framework of the present invention, it was also surprisingly found that the final calcining is particularly advantageously carried out for less than 5 hours at a temperature of from 660° C. to 850° C., in particular for 1 to 4 hours from 680° C. to 800° C. As a result of this comparatively short final calcining at high temperatures, the acidity of the acid centres of the catalyst can clearly be advantageously influenced and the stability of the catalyst according to the invention simultaneously increased. It was also found that this advantageous "intensified" final calcining also has positive effects on the catalytic properties of the aluminosilicate-based catalyst in the case of other aluminosilicate catalysts when (any) other aluminium, alkali and silicon sources of any templates as well as binders not according to the invention are used.

The thus-obtained end-product can, as mentioned above, be particularly advantageously used in CMO processes, particularly preferably MTP processes.

The present invention also relates to a process for producing olefins from oxygenates, preferably methanol, dimethyl ether or mixtures thereof, wherein the educt gas, i.e. gaseous starting material, is passed over a catalyst according to the invention. By oxygenates is meant within the framework of the present invention oxygen compounds, in particular organic oxygen compounds such as alcohols and ethers. In addition to oxygenate, the gaseous starting material can also contain water vapour. Here, the educt gas is preferably passed over a catalyst according to the invention in a catalyst cycle of over 370 hours. The process according to the invention for producing olefins from methanol preferably takes place at temperatures in the reactor of between 380° C. and 550° C., still more preferably between 420° C. and 510° C., wherein the WHSV (weight hourly space velocity) is preferably in the range of from 0.25 to 5 $h^{-1}$, still more preferably 0.4 to 3 $h^{-1}$, and particularly preferably in the range of from 0.5 to 1.5 $h^{-1}$.

The invention is explained in more detail by the non-limitative examples below.

DESCRIPTION OF THE FIGURE

FIG. 1 shows the catalytic properties of the spherical catalysts according to the invention compared with catalysts in the form of extrudates. The methanol conversion rate under the following conditions in the isothermal reactor is shown: $T^R_{OUT}$ (temperature of the reactor at the outlet=450° C.; load:WHSV=1 $h^{-1}$ (kg methanol/kg catalyst and hour), weight ratio (MeOH:$H_2O$)=1:2.

METHODS

The following methods are used to determine the parameters of the catalysts according to the invention:
1. Diameter of the primary crystallites:
    The quoted values for the primary crystallites are the average dimensions (arithmetic mean of the largest and the smallest dimensions, averaged over a plurality of crystallites, preferably at least 25 crystallites are used). These values are determined with a LEO Field Emission Scanning Electron Microscope (LEO Electron Microscopy Inc., USA) using powder samples of the catalyst which had previously been redispersed in acetone, treated with ultrasound for 30 seconds and then deposited on a carrier (Probe Current Range: 4 pA to 10 nA). The measurement is customarily carried out at a magnification of 20,000 (magnifications of 80,000 or also 10,000 are also suitable). The values were able to be confirmed at a magnification of 253,000.
2. Average diameter of the spheres of the catalyst:
    With the help of a sliding calliper, at least 25 spheres are selected from a representative sample and their diameter determined by hand. The average diameter is then calculated from the 25 individual measurements.
3. Pore diameter:
    The pore diameter is obtained using the mercury porosimetry method in accordance with DIN 66133.
4. Pore volume:
    The pore volume is determined using the mercury porosimetry method in accordance with DIN 66133.
5. BET surface area:
    The BET surface area is determined according to the BET method in accordance with DIN 66131; a publication of the BET method is also found in J. Am. Chem. Soc. 60, 309 (1938).

EXAMPLES

Comparison Example A

A catalyst was produced according to Example 1 of EP 1 424 128 with an average diameter of the primary crystallites of approximately 0.03 μm (Si/Al ratio 105). The process given there and the physical and chemical properties of the product are expressly incorporated by reference into the present description.

Thus according to this comparison example, aluminosilicate zeolites with a primary crystallite size of <1 μm were produced. The catalysts were produced as binders with the addition of aluminium oxide.

In particular, the procedure was as follows:

A reaction mixture was produced by intimate mixing of two solutions at room temperature in a 40-liter autoclave. The two solutions were called solution A and solution B. Solution A was produced by dissolving 2218 g TPABr in 11 kg deionized water. 5000 g of a silicic acid customary in the trade was added to this solution. Solution B was produced by dissolving 766 g NaOH and then 45.6 g $NaAlO_2$ in 5.5 liters of deionized water. The still warm solution B was added to solution A. The autoclave was then closed and taken immediately to the reaction temperature accompanied by stirring at approximately 60 rpm. The reaction was ended once the average diameter of the primary crystallites was 0.03 μm. After cooling, the autoclave was opened, the product removed from the reaction vessel and filtered. The filter cake was suspended in approx. 40 liters of deionized water, mixed with approximately 5 liters of a 0.4 wt.-% aqueous suspension of a flocculant customary in the trade, followed by decanting after stirring and settling of the pre-agglomerates of the solid. The described wash process was repeated until the wash water had a pH of 7 to 8 and a Br concentration of less than 1 ppm. The suspension in which pre-agglomerates of primary crystallites were to be seen, which were clearly held together by the flocculant, was filtered. The filter cake was then dried at 120° C. for 12 hours.

The dried filter cake was reduced to a particle size of 2 mm with a granulator customary in the trade.

The granules were taken to 350° C. at a heating rate of 1° C./min under nitrogen (1000 Nl/h) and calcined at 350° C. for 15 hours under nitrogen (1000 Nl/h). The temperature was then taken to 540° C. at a heating rate of 1° C./min and the granules were calcined in air for 24 hours at this temperature in order to burn off the remaining template.

The calcined Na zeolite was suspended in 5 times the quantity of a 1-molar aqueous HCl solution and taken to 80° C. Stirring was carried out at this temperature for an hour. Then approximately 1 liter of a 0.4 wt.-% suspension of the flocculant was added, and the supernatant acid was decanted after the solid had settled. The thus-described procedure was repeated once more.

In approximately 10 wash procedures the solid was suspended each time in 60 liters of deionized water accompanied by stirring and mixed with an average of 100 ml of a 0.4 wt.-% suspension of the flocculant. After the zeolite had settled, the remaining solution was decanted. When the level of Cl$^-$ in the wash water was <5 ppm, the suspension was filtered off and dried for 15 hours at 120° C.

The dried H zeolite was reduced to 2 mm with a granulator customary in the trade and taken to 540° C. in air at a heating rate of 1° C./min and calcined in air for 10 hours at this temperature.

5000 g of the calcined H zeolite produced as described above were ground with the help of a laboratory mill to a particle size of approximately 500 μm and mixed dry for 15 min in a double-Z kneader with 1470 g of a peptizable hydrous aluminium oxide customary in the trade with a particle size distribution of from 98 wt.-%≤90 μm; 95 wt.-%≤45 μm and 55 wt.-%≤25 μm. 4565 ml of a 1.5 wt.-% aqueous acetic acid solution (for peptizing the hydrous aluminium oxide) and 417 ml steatite oil were added slowly to this mixture.

This mixture was kneaded for approximately 30 min until plasticization set in and extruded in an extruder customary in the trade to form cylindrical shaped bodies with a diameter of approximately 1.5 mm and a length of approximately 3 mm. The final calcining was carried out for 3 hours at 650° C.

The composition of the cylindrical extrudate from comparison example A is given in Table I.

Example B 1000 g of a calcined and ground H zeolite produced analogously to that described above under comparison example A (using the quantities of starting substances given in Table 1) were mixed in an Eirich mixer with 1106 g of an aqueous colloidal silicon dioxide dispersion over a period of approx. 1 hour (RT to 45° C., stirring speed used up to a max. of 1375 rpm). The spherical product that formed during this mixing procedure is then dried for 16 hours at 60° C. in a high-temperature oven and calcined for 5 hours at 600° C.

The composition of the spherical catalyst according to the invention from Example B is given in Table I.

Example C 1500 g of a mixture of zeolite powder (the calcined and ground H zeolite produced as described above under comparison example A) with 2.0 wt.-% burnout substance (polyvinylidene chloride-acrylonitrile polymers) were introduced into an Eirich mixer. To moisten the material, a binder dispersion of dispersed peptizable hydrous aluminium oxide and water was added (rotational speed of the whirler at 1500 rpm). When sufficient liquid had been added, granules began to form. A granulation to form spheres was achieved by alternately adding pre-mixed zeolite powder with burnout substance and binder dispersion. In total, 822 g binder dispersion and 515 g mixture of zeolite powder with burnout substance were additionally introduced. The spheres were then dried and calcined.

The composition of the spherical catalyst according to the invention from Example C is given in Table I. The catalytic activity of the spherical catalyst according to the invention from Example C is shown in FIG. 1 using experimental data.

Comparison Example 1D 60 kg hydrous aluminium oxide was mixed with 64 kg water in a double segment kneader. 72.3 kg of a 30 wt.-% aqueous nitric acid solution (to peptize the hydrous aluminium oxide) was added to this mixture. After 60 min mixing, 250 kg zeolite powder (the calcined and ground H zeolite produced as described above under comparison example A) was added to the homogeneous material. 29 kg water was then added to the powdery material until plasticization set in and 21 kg steatite oil and mixing carried out again. In a double-shaft extruder, the material was extruded to form cylindrical shaped bodies with a diameter of approximately 3.2 mm and a length of approximately 6 mm. The final calcining was carried out for 5 hours at 580° C.

The composition of the cylindrical extrudate from comparison example D is given in Table I. The catalytic activity of this catalyst from comparison example D is shown in FIG. 1 using experimental data.

TABLE I

| | Comparison example A | Example B | Example C | Comparison example D |
|---|---|---|---|---|
| Molar ratio of the starting substances | | | | |
| $SiO_2$ | 100 | 100 | 100 | 100 |
| $NaAlO_2$ | 0.67 | 2 | 0.67 | 0.67 |
| NaOH | 23 | 23 | 23 | 23 |
| TPABr | 10 | 10 | 10 | 10 |
| $H_2O$ | 1100 | 1100 | 1100 | 1100 |
| Crystallization data | | | | |
| Temperature (° C.) | 130 | 130 | 130 | 130 |
| Time (h) | 23 | 23 | 23 | 23 |
| Crystallinity (%) | 100 | 100 | 100 | 100 |
| Primary crystallite size (μm) | 0.03 | 0.03 | 0.03 | 0.03 |
| Chem. and phys. properties of the catalyst | | | | |
| Binder | pept. $Al_2O_3$ | $SiO_2$ | pept. $Al_2O_3$ | pept. $Al_2O_3$ |
| Si/Al atomic ratio | 105 | 45 | 105 | 105 |
| BET surface area (m$^2$/g) | 385 | 360 | 394 | 335 |
| Pore volume (cm$^3$/g) | 0.46 | 0.35 | 0.30 | 0.33 |
| Average diameter of the spheres (mm) | — | 3.1 | 3.3 | — |
| Pore volume distribution - proportion of pores with diameter 14 to 1750 nm | 88% | 80% | 88% | 81% |

Application Example

This application example shows the advantages of the catalyst according to the invention using catalytic data of the CMO process (conversion of methanol to olefins) in an isothermal fixed-bed reactor.

The tests were carried out as in application example 1 of EP 0 369 364 B1, the disclosure therein regarding same is incorporated by reference into the present description. FIG. 1 shows the catalytic properties of the spherical catalyst according to the invention compared with the catalyst in the form of extrudates. The methanol conversion rate under the following conditions in the isothermal reactor is shown: $T^R_{OUT}$ (temperature of the reactor at the outlet=450° C.; load:WHSV=1 $h^{-1}$ (kg methanol/kg catalyst and hour), weight ratio (MeOH:$H_2O$)=1:2. The methanol/water feed was passed over the CMO catalyst in an isothermal fixed-bed reactor with a WHSV of 3 (kg/(kg×h), i.e. kilogram total feed per kilogram of catalyst and per hour at a pressure of 1 bar for the conversion of methanol. Gas phase and liquid phase at the outlet of the CMO catalyst reactor were determined with the customary gas-chromatography analysis methods.

FIG. 1 shows the clearly improved activity of the spherical catalyst according to the invention. In particular, it is shown that the life in the cycle of the catalyst according to the invention is much increased compared with an extrudate catalyst, considering the significantly better methanol conversion rates after a cycle duration of 370 h.

The catalysts (also the catalyst according to the invention) can be regenerated after a first cycle ends by first stopping the MeOH stream. Nitrogen is then fed in to expel the remaining MeOH. Finally, oxygen is slowly added to the nitrogen in gradually increasing concentrations in order to burn off the hydrocarbon deposited on the catalysts. The regeneration of the catalysts is ended when the oxygen content of the nitrogen stream is the same at the inlet and at the outlet of the catalyst bed.

The invention claimed is:

1. A catalyst comprising pentasil-type aluminosilicates and a binder, wherein the catalyst is in the form of granulated spheres with an average diameter between 0.3 and 7 mm, wherein the BET surface area of the catalyst is between 360 and 600 $m^2/g$, wherein the spheres of the granulated spherical catalyst comprise primary crystallites with an average diameter of at least 0.01 μm and less than 0.1 μm.

2. The catalyst according to claim 1, wherein the binder comprises an inorganic oxide.

3. The catalyst according to claim 1, wherein the pore volume of the catalyst is 0.2 to 0.8 $cm^3/g$.

4. The catalyst according to claim 1, wherein the quantity of the binder comprises 5 to 60 wt.-%, relative to the total weight of the aluminosilicate and the binder.

5. The catalyst according to claim 1, wherein at least 10% of the pores of the catalyst have a diameter between 14 and 1750 nm.

6. The catalyst according to claim 1, wherein the catalyst is dried and in calcined H form.

7. The catalyst according to claim 1, wherein the aluminosilicate has a Si/Al atomic ratio of approximately 50 to 250.

8. The catalyst of claim 1 wherein at least 10% of the pores of the catalyst have a diameter between 80 and 1750 nm.

9. A process for producing the catalyst of claim 1 comprising mixing a binder with pentasil-type aluminosilicates, to form a mixture, wherein primary crystallites of the aluminosilicates have an average diameter of at least 0.01 μm and less than 0.1 μm, shaping the mixture into spheres with an average diameter of between 0.3 and 7 mm to form a shaped product, and drying and calcining the shaped product to form the catalyst.

10. The catalyst of claim 1 wherein the quantity of the binder comprises 10 to 40 wt. %, relative to the total weight of the aluminosilicate and the binder.

11. The process of claim 9 further comprising adding a burnout substance to the mixture.

12. Process for producing olefins from oxygenates, comprising passing said oxygenates over the catalyst according to claim 1.

* * * * *